United States Patent [19]

Edwards

[11] 4,126,417
[45] Nov. 21, 1978

[54] MEANS FOR TESTING AND TREATMENT OF SOIL IN WHICH A PLANT IS GROWING

[76] Inventor: Paul R. Edwards, 4407 Tortilla Cir., Oceanside, Calif. 92054

[21] Appl. No.: 557,392

[22] Filed: Mar. 11, 1975

[51] Int. Cl.² .................. G01N 21/06; G01N 21/08
[52] U.S. Cl. ........................ 422/56; 23/230 R; 47/1 R; 422/57; 422/61
[58] Field of Search ............ 23/253 TP, 230 R, 259; 47/1 R, DIG. 10

[56] References Cited

U.S. PATENT DOCUMENTS

| | | | |
|---|---|---|---|
| 1,238,123 | 8/1917 | Freeman | 23/253 TP |
| 2,787,238 | 2/1957 | Luce | 23/253 TP |
| 3,019,638 | 2/1962 | Klein | 73/73 |
| 3,572,997 | 3/1971 | Burk | 23/253 TP |
| 3,702,755 | 11/1972 | Palmer | 23/253 TP |
| 3,881,873 | 5/1975 | Klowden | 23/253 TP |

Primary Examiner—R.E. Serwin

[57] ABSTRACT

A testing and treatment kit, a soil testing device and a procedure adapted for the home owner, especially for raising plants in containers. A stick having a pH-testing coating on one side and a nitrate-testing coating on the other side, the coatings changing colors during testing and being juxtaposed to colored sections for matching purposes to determine pH and nitrate levels. The ket including color-coded nitrate-increasing and acid-increasing pills, as well as color-coded fungicide and insecticide pills. The colored sections having indicia indicating the numbers of nitrate and acid pills to be added to a given quantity of water to produce solutions used in watering the soil properly correcting nitrate and acid soil conditions.

10 Claims, 2 Drawing Figures

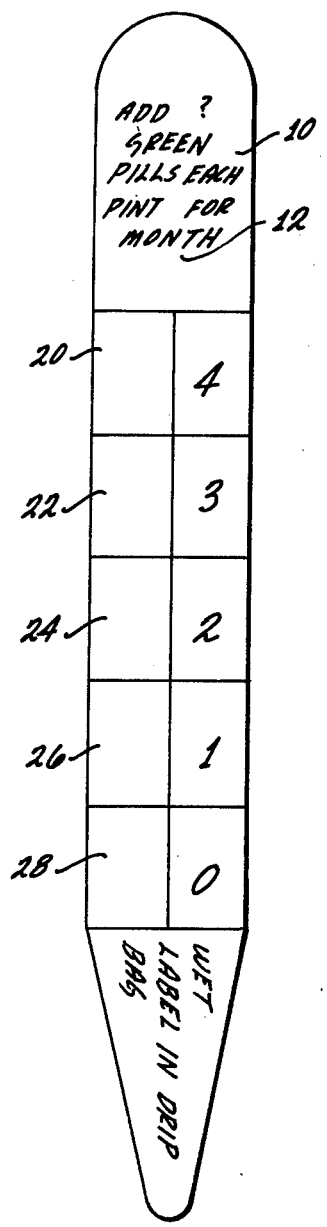
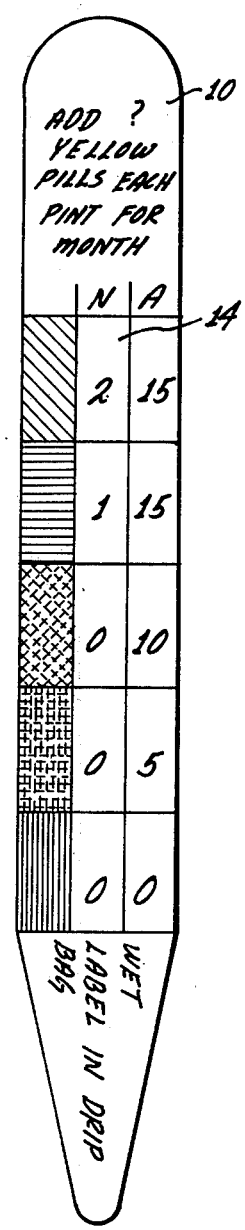

MEANS FOR TESTING AND TREATMENT OF SOIL IN WHICH A PLANT IS GROWING

BRIEF SUMMARY OF THE INVENTION

My invention relates to means to assist the home owner in growing plants in a container from which effluent may be obtained in which seven special, interrelated materials are required in addition to water. They are: (1) a growing media, (2) a fertilizer, (3) an acidifier, (4) a nitrate indicator, (5) a pH indicator, (6) an insecticide, and (7) a fungicide.

The media is very special in that it (a) contains no fertilizer other than that in the limestone used for pH correction, (b) contains no quickly rotable organics such as peanut hulls, corncobs, sawdust, manure or sedge peat moss, (c) it contains no fine clay or the like which would cloud the effluent. It must (1) drain quickly, (2) retain enough water so that watering is not required frequently, (3) contain enough air immediately after being drained that it will support plant growth.

The fertilizer, acidifier, insecticide, and fungicide are supplied in measured quantities, such as a pill, such quantity being that amount required in every pint of water used to saturate the media and recover one half of that applied as effluent.

Materials preferably are color-coded for convenience and safety, i.e., the fertilizer may be green, the acidifier yellow, the insecticide red, and the fungicide blue.

The two testing means are similar in that each requires a wettable paper, or the like, with preferably five colors on each of them. Opposite the colors are strips which will change color according to the amount of nitrate in the effluent or the pH of the effluent tested. This color will match one of the five original colors. The number on the strip at the point where original color and test produced color match is the number of pills required to return the media to the correct nitrate or the correct pH concentration desired by the plants being grown in that container.

The testing for Nitrate and the test for pH are done periodically, such as monthly, but the number of pills indicated by the tests are included in each pint of water used during the month following the tests.

The insecticide and the fungicide are applied at intervals. The insecticide monthly and the fungicide every other month unless insects or fungi are observed. They are to be used on ornamentals only.

BACKGROUND OF THE INVENTION

Plant growing means presently used do not allow close regulation of the fertilizer and pH content of the media. This invention because of the materials used and because of the simplicity with which they are used permits the average housewife or other person usually inexperienced in plant growing to succeed.

Because the media presently used do not drain sufficiently to allow enough air to enter, or do not permit an effluent to remove excess fertilizer and other soil salts; and because these media decompose to produce ammonia and nitrites which are poisonous to plants in other than very small amounts; and because these products of decomposition may be converted to a nitrate at a time when additional nitrates are not desired, they are poorly suited for growing plants, especially when using the testing system of this invention, in comparison to the media of the present invention which is designed to avoid all of these faults. Other materials such as perlite and redwood sawdust could be substituted. However, manure, peanut hulls, corncobs, etc., could not be substituted because they rot too quickly.

The fertilizers presently supplied do not contain all of the elements plants are known to require. Formerly this did not often prove detrimental as the growing media used in containers were basically better supplied with minor elements than the present soil mixes which are composed primarily of peat, vermiculite, sponge rock, bark, and other wood products. The fertilizers formerly supplied had many minor elements in the form of impurities and their importance was not fully realized until high analysis fertilizers with few impurities were placed on the market. Most of these high analysis fertilizers presently supplied contain urea and ammonia salts as their source of nitrogen. These must be converted to nitrate nitrogen before they are available for use by plants. Often because of the lack of sufficient air, excess moisture, lack of bacteria to convert the urea to ammonia, to nitrite, to nitrate; or the ammonia, to nitrite, to nitrate, the ammonia and nitrite accummulate to damaging amounts; and, also because the urea and ammonia do not become nitrate under these conditions, the plant is starved for the lack of it. The fertilizer of the present invention avoids this conversion problem by supplying nitrogen in the nitrate form only. Also, the fertilizer of the present invention supplies the sixteen or so elements thought to be essential for plant growth and in the ratio to nitrogen which they are thought to be necessary. Because in the present invention fertilizer is supplied in all water used on the basis of the nitrate test of the effluent which is the same as in the soil solution, all elements remain available to the plant in the original correct ratios.

The fertilizers presently supplied neither contain sufficient surfactant to wet the media nor sufficient sequestrening or chelating agents to dissolve the precipitated salts left in the media by previous fertilizing, by the water used, or by media decomposition. By supplying surfactants, sequestering and chelating agents in large quantities and in sufficient water at each and every watering to produce an effluent equal to one-half of the water applied, these waste products do not accummulate.

When using the present fertilizers the phosphates as well as iron and other metals are especially vunerable to precipitation when they enter the growing media. For this reason in this invention, in addition to using sequestering and chelating agents, we use those compounds of these elements which are not easily precipitated. For example: glycerophosphate and a small amount of technical sodium ferric diethyl-enetri-amine pentaacetate.

Soil testing kits as presently offered for home use are outgrowths of those kits originally offerred to and used by nursery and greenhouse operators. These kits are considered by most home owners to be too difficult to use. They involve using a solution to wet the soil which will extract the elements being tested for, a filter paper to remove sediment, another solution to add to the filtrate and a color chart to compare with the resulting color of the filtrate to indicate the amount of the element present. Even for those homeowners who can get this far, the final decision of how much fertilizer, of what composition, to add to the size of the area involved was usually impossible for them to calculate. As the simplest test kits required testing for four things — pH, Nitrate, Phosphate and Potash, four quantity calcultations were required and this did not correct for the other 13 elements needed by plants. The nitrate test used does not indicate ammonia or urea which are almost always present because they are usually in the fertilizers being used and so this test gave no true indication of the actual nitrogen bearing materials present — although not at that moment available to the plant.

In fact, because of the reaction between chemicals, addition of one element would change the availability of another. Also, the specific separate fertilizer elements needed are not generally available to the home owner and when available are usually not in the more desirable soluble forms.

The fertilizer and media of the present invention will prevent these interactions, and because all elements are supplied in the right ratio, and without urea and ammonia, only nitrate and pH need be tested for. Because the surfactant, chelating, sequestering and excess water over what is required to wet the media will remove any excess minerals from the media so they can be disposed of with the effluent there will be no build up of salts in the media. Periodic tests of the effluent for nitrate and pH by simply wetting the test strips with the effluent and with the regular addition of that number of fertilizer pills and pH pills indicated by the tests optimum conditions will be maintained in the media for plant growth. As the plant grows, days shorten, temperatures fall, and other environmental conditions take place varying amounts of fertilizers are consumed, and new tests will be required so that a new rate of using fertilizer pills and pH pills can be established. After a few tests at 1 month intervals, the homeowner should be able to determine if more or less frequent tests are required.

The insecticides on the market are mostly in spray or aerosal form and therefore do not obtain complete wetting of the plant and are dangerous to the applicator, if inhaled, or to the plant if the aerosal is held close enough to freeze it. Some are in granular form and therefore difficult to apply to container plants which often occupy the entire soil surface. By supplying a systemic insecticide in a soluble pill form for easy accurate measuring and using enough water to completely saturate the growing media the safety of the applier and better control of insects is assured. Several materials are planned in combination for a wide range of insect control. Aldicarb (Temik) against mites, and Acephate (Orthene), against aphids, etc., are contemplated combinations when label clearance for such use is obtained.

Fungicides are rarely used on plants in the home because fungus damage is not recognized, except for mildew. By supplying a pill which a mixture of three systemic fungicides one of which will control mildew, the novice will be able to grow most plants some of which were formerly considered too difficult. Meterials to be used are Trifluorine, for mildew, rust and leaf spots; Truban (Ethazol) for pithium and phytophthora; and Benomyl (Benlate) for rhizoctonia, fusarium, sclerotinia and botrytis.

DESCRIPTION OF THE PREFERRED EMBODIMENTS

My invention will be understood from the following description, read with reference to the drawings, in which:

FIG. 1 is a view of one face of a soil testing device which forms a part of a specific embodiment of my invention.

FIG. 2 is a view of the opposite face of the device.

The plant growing media preferably is composed of equal parts by volume of granulated clay particles ⅛ inch to 3/16 inch diameter, Vermiculite ⅛ inch to 3/16 inch diameter, and spagnum peat-moss. Its acidity is adjusted with dolomite limestone to pH 6.5. It has an air capacity after saturation and drainage of water of 32% to 35%; a water availability based on volume of 42% to 45%; a water percolation rate of 60+ inches per hour; it has a weight of 33 lbs. to 35 lbs. per cu. ft., good ion exchange ability and good physical decomposition stability.

The fertilizer in the form of a color-coded pill supplies a pH of 6.5 and 100 ppm nitrate in 1 pint of water and contains 15 elements in the following ratio and minimum amounts: N, 8.%; P, 2.%; K, 4.%; Ca, 4.%; Mg, 0.50%; S, 1.00%; B, 0.02%; Cl, 0.10%; Co, 0.0005%; Cu, 0.05%; Fe, 0.10%; Mn, 0.05%; Mo, 0.0005%; Zn, 0.05%; & Na, 0.10%. These elements are derived from potassium nitrate, ammonia free calcium nitrate chelate, glycerophosphate, magnesium sulfate, potassium chloride cobalt sulfate sequestrene, chelate, copper sulfate sequestrene chelate, ferrous sulfate sequestrene chelate, manganese sulfate sequestrene chelate, zinc sulfate sequestrene chelate, anhydrous sodium molybdate and sodium borate. Also additional sufficient chelating agents, such as EDTA, HEDTA, and DTPA to prevent precipitation by reaction of compounds within the fertilizer solution; and sufficient surfactants for soil wetting.

The color-coded acid pills reduce one pint of distilled water to pH 6. They are composed of aluminum sulfate, ferrous sulfate and a small amount of pure phosphoric acid, $(H_3PO_4)$. The device 10 shown in the drawings has a first face 12 concerned with nitrate testing and a second face 14 concerned with pH testing. In FIG. 1, the colors are not adapted to be handled completely by lining the drawing for colors, and area 20 is red, area 22 is red-orange, area 24 is orange, area 26 is gold, and area 28 is yellow. In FIG. 2 the colors are shown by lining the drawing. The green represents a pH of 7.5, the blue a pH of 7.0, the orange a pH of 6.5, the gold a pH of 6.0, and the pink a pH of 5.5.

In this invention the testing means for nitrate is designed to maintain the soil solution with around 600 ppm nitrate for an established plant. A strip of paper which is color sensitive to nitrate is printed with a color chart and a series of numbers. See drawing FIG. 1. When wet with a nitrogen containing effluent it changes color depending on the amount of nitrate present. I will give examples of color changes. The color 'yellow' is associated with the numeral '0'. This indicates sufficient nitrate is present. Gold, (1) indicates that one pill is required, Orange, (2) indicates two pills are required. Orange-red, three pills and red, four pills. It is unlikely over 4 pills would be necessary to maintain rapid growth because the soil does have some absorptive ability and to add more at one time would be potentially dangerous to the plant.

The testing means for pH is designed to regulate the pH of the media at two levels, pH 6.5 and pH 5.5. See drawing FIG. 2. It is made by printing on pH sensitive paper a color chart of five colors with two rows of numbers opposite them. At the top of one row of numbers is the letter N and at the top of the other row of numbers is the letter A. N designates that these numbers are the number of pills required for normal soil loving plants and the A list is for the acid loving plants. The number used is determined by observing the number nearest the matching colors of the color chart and the color developed by wetting the paper in effluent from the container of plants being watered. Best results are obtained by using a small amount of the total effluent obtained, which should be one-half of the total applied to the container. The test charts are conveniently attached to opposite sides of a small flat stick about 6 inches long.

The insecticide is conveniently a red colored pill of such size that one in each pint of all water applied at one application will be absorbed by the plant and kill all insects on the plant or in the soil. It will be a mixture of several insecticides, an adjuvant, and a surfactant. The exact chemicals and their ratio's are not a part of this disclosure but the above and the fact that they are conveniently color coded, sized for each pint of water, systemic, non-toxic to most plants and a mixture to control all types of insects and nematodes is claimed. Materials such as Aldicarb and Acephate are planned.

The fungicide is conveniently a blue color coded pill, sized one for each pint of water applied at one application, non-toxic to most plants, has broad fungicidal properties and low mammilian toxcity, is biodegradable, does not change the ph of the soil solution, systemic by soil application, contains an adjuvant and a surfactant. Fungicides such as Triforine, for mildew, rust and leaf spots; Truban (Ethazol) for pithium and phytophthora; and Benomyl (Benlate) for rhizoctonia, fusarium, sclerotinia, and cotrytis are to be used.

It is apparent from the foregoing that there is provided according to the present invention a new and novel plant growing means in the form of precisely measured and conveniently color-coded materials, and a way of applying them which eleminates the problems of salt build up from fertilizer, soil, or water, and two testing devices which are easy to use and the results to follow, so that unskilled persons can safely and consistently succeed in growing plants by this method.

The mention of chemicals or trade names is not intended to imply that these exact materials will be used for the purpose mentioned but it is intended to illustrate the way in which the problem is to be overcome.

It is obvious that many modifications could be made within the scope of the invention without departing from the principals involved and the invention includes all such modifications.

USE OF THE SYSTEM

1. Select a container that will drain quickly.
2. Place a filter of burlap, cotton batting, or the like, over the bottom drain holes.
3. Fill the container with the planter mix of this invention.
4. Plant plants firmly but do not pack soil. If plants have soil on roots, examine closely. If it is primarily of calcined clay particles, sand, spagnum peat, vermiculite, sponge rock, redwood sawdust, or other material that will not rot quickly, it should be left on the roots. If it is of a material which will rot quickly, gently remove.
5. Obtain the amount of water which the container would hold without any media in it.
6. Set the container on another container without holes in its bottom.
7. Check the pH list supplied for the pH desired by the plant being planted. If the plant desires normal soil (pH 6.5) it will be indicated by N on the list. If it prefers acid soil (pH 5. to 5.5) it will be indicated by A on the list.
8. If the plant requires normal pH add two fertilizer pills in each pint of water obtained in (5) above. If plant is acid loving, add five acid pills also to each pint of water obtained in (5) above. Slowly apply this water to the surface of the container at several locations to settle the soil about the plants roots and completely saturate it.
9. Catch the water in the container mentioned in (6) above. This water should be equal to one-half of that applied. If not additional water prepared as in (8) above should be applied until such amount is recovered.
10. Observe moisture content of media daily. When it approaches the dry side, but is still not dry, more of the solution as in (8) above should be applied until one-half of it is recovered. Plants vary in their desire for moisture so this approach toward the dry side will vary. Their moisture preference is also indicated on the pH list.
11. Continue this practice as in (10) until 1 month has passed.
12. At the end of 1 month dip a test stick in the water recovered. Be sure the container in which it is recovered is clean. The test stick has a pH test on one side and a nitrogen test on the other.
13. Check for matching colors and mark on the test stick which they are with a waterproof pen or pencil.
14. Stick this test stick into the soil of the pot tested where it can be seen for reference.
15. Each time moisture is required for the next month use the quantity of green fertilizer pills and the quantity of yellow acid pills which was indicated by the matching colors in each pint of water used.
16. The use of the blue fungicide pills should start with the second watering and should be repeated every 2 or 3 months, or as needed. It is added with the green and yellow pills required at that watering. One-half of the water should be recovered.
17. The use of the red insecticide pills should be delayed until the end of the first month and applied with the newly determined rate for Nitrogen and pH pills unless insects are observed prior to that time. They should be repeated each month.
18. The blue fungicide pills and the red insecticide pills should not be applied at the same time or during adjacent waterings.
19. Be sure the soil is not dry at the time any water containing pills is applied. If it is dry, apply water only for that watering only, and resume the proper procedure when the proper moisture content is obtained. Do not apply an excess of clear water.

Do not be alarmed if at the end of the first month the number of pills required is doubled. This is normal. The quantity used in following months will probably also be increased slightly.

What is claimed is:

1. A soil testing and treatment kit useable relative to soil in which a plant is growing, comprising:
    (a) a piece of material forming a pH soil tester having two juxtaposed areas differently treated, a first of said two areas having a chemical treatment so as to change to various colors responsive to pH level of any liquid to which said first area is exposed, the second of said two areas being treated by coloring several sections of said second area different colors corresponding to said various colors to which said first area would turn depending on said pH level,
    (b) separately packaged quantities of acid-increasing material, and (c) numerical indicia on said piece of material indicating relative to each differently colored section of said second area the number of said quantities of said acid-increasing material that would be required to add to a given quantity of liquid to provide the proper acidic strength to treat said soil to produce the desirable soil pH if said soil initially had a pH level related to the change of color of said first area of said piece of material.

2. The subject matter of claim 1 in which said numerical indicia indicates two separate numbers of said quantities of said acid-increasing material relative to each differently colored section of said second area so as to indicate different recommended treatment for soil having plants preferring normal soil and for soil having plants preferring acid soil.

3. The subject matter of claim 1 in which said kit includes means providing thrid and forth juxtaposed areas differently treated, said third area having a chemical treatment so as to change to various colors responsive to nitrate level of any liquid to which said third area is exposed, said fourth area being treated by coloring several sections of said fourth area different colors corresponding to said various colors to which said third area would turn depending on said nitrate level, separately packaged quantities of nitrate-increasing material, and numerical indicia on said means providing said third and fourth areas indicating relative to each differently colored section of said fourth area the number of said quantities of said nitrate-increasing material that would be required to add to a given quantity of liquid to provide the proper nitrate strength to treat said soil to produce the desirable soil nitrate level if said soil initially had a nitrate level related to the change of color of said third area.

4. The subject matter of claim 3 in which said quantities of acid-increasing material and of nitrate-increasing material have the form of pills and in which the acid-increasing pills are differently colored than said nitrate-increasing pills.

5. The subject matter of claim 4 in which said kit also contains differently color-coded fungicide and insecticide pills.

6. A soil testing and treatment kit usuable relative to soil in which a plant is growing, comprising:
(a) a piece of material forming a nitrate soil tester having two juxtaposed areas differently treated, a first of said two areas having a chemical treatment so as to change to various colors responsive to nitrate level of any liquid to which said first area is exposed, the second of said two areas being treated by coloring several sections of said second area different colors corresponding to said various colors to which said first area would turn depending on said nitrate level,
(b) separately packaged quantities of nitrate-increasing material, and
(c) numerical indicia on said piece of material indicating relative to each differently colored section of said second area the number of said quantities of said nitrate-increasing material that would be required to add to a given quantity of liquid to provide the proper nitrate strength to treat said soil to produce the desirable soil nitrate level if said soil initially had a nitrate level related to the change of color of said first area of said piece of material.

7. A growing medium testing and treatment device usable relative to a medium in which a plant is growing, comprising:
(a) a piece of material forming a pH tester having two juxtaposed areas differently treated, a first of said two areas having a chemical treatment so as to change to various colors responsive to pH level of any liquid to which said first area is exposed, the second of said two areas being treated by coloring several sections of said second area different colors corresponding to said various colors to which said first area would turn depending on said pH level, and
(b) numerical indicia on said piece of material indicating relative to each differently colored section of said second area the strength of acid-increasing material that would be required to properly treat said medium to produce the desirable growing medium pH if said medium initially had a pH level related to the change of color of said first area of said piece of material.

8. The subject matter of claim 7 in which said numerical indicia indicates two separate strengths of said acid-increasing material relative to each differently colored section of said second area so as to indicate different recommended treatment for growing medium having plants preferring normal soil and for growing medium having plants preferring acid soil.

9. The subject matter of claim 8 in which said piece of material is a stick-like article having said two juxtaposed areas on one side and on the other side having third and fourth juxtaposed areas differently treated, said third area having a chemical treatment so as to change to various colors responsive to nitrate level of any liquid in which said third area is exposed, said fourth area being treated by coloring several sections of said fourth area different colors corresponding to said various colors to which said third area would turn depending on said nitrate level, and numerical indicia on said other side of said stick-like article indicating relative to each differently colored section of said fourth area the strength of nitrate-increasing material that would be required to properly treat said growing medium to produce the desirable growing medium nitrate level if said growing medium initially had a nitrate level related to the change of color of said third area.

10. A growing medium testing and treatment device usable relative to a medium in which a plant is growing, comprising:
(a) a piece of material forming a nitrate tester having two juxtaposed areas differently treated, a first of said two areas having a chemcial treatment so as to change to various colors responsive to nitrate level of any liquid to which sad first area is exposed, the second of said two areas being treated by coloring several sections of said second area different colors corresponding to said various colors to which said first area would turn depending on said nitrate level, and
(b) numerical indicia on said piece of material indicating relative to each differently colored sections of said second area the strength of nitrate-increasing material that would be required to properly treat said growing medium to produce the desirable growing medium nitrate level if said growing medium initially had a nitrate level related to the change of color of said first area of said piece of material.

* * * * *